(12) United States Patent
Woolard et al.

(10) Patent No.: US 10,006,848 B2
(45) Date of Patent: Jun. 26, 2018

(54) CONTAINMENT HOUSING WITH INTEGRATED TEST AEROSOL INJECTION AND SAMPLING

(71) Applicant: CAMFIL USA, INC., Riverdale, NJ (US)

(72) Inventors: Keith G. Woolard, Washington, NC (US); Larry E. Bland, Jr., Washington, NC (US)

(73) Assignee: CAMFIL USA, INC., Riverdale, NJ (US)

( * ) Notice: Subject to any disclaimer, the term of this patent is extended or adjusted under 35 U.S.C. 154(b) by 314 days.

(21) Appl. No.: 14/871,250

(22) Filed: Sep. 30, 2015

(65) Prior Publication Data
US 2016/0097706 A1    Apr. 7, 2016

Related U.S. Application Data

(60) Provisional application No. 62/059,578, filed on Oct. 3, 2014.

(51) Int. Cl.
*G01M 3/20* (2006.01)
*G01N 15/08* (2006.01)
*G01N 1/22* (2006.01)

(52) U.S. Cl.
CPC ............ *G01N 15/082* (2013.01); *G01M 3/20* (2013.01); *G01N 15/0806* (2013.01);
(Continued)

(58) Field of Classification Search
CPC ...... G01M 3/04; G01M 3/20; G01N 15/0806; G01N 15/082; G01N 2015/084;
(Continued)

(56) References Cited

U.S. PATENT DOCUMENTS 4,055,075 A * 10/1977 Allan ................. B01D 46/0013
                                                            239/3
4,324,568 A    4/1982 Wilcox et al.
(Continued)

OTHER PUBLICATIONS

Search Report and Written Opinion of the International Seaching Authority for PCT/US2015/053396 dated Jan. 29, 2016 (8 pgs.)
(Continued)

*Primary Examiner* — Blake A Tankersley
(74) *Attorney, Agent, or Firm* — Patterson + Sheridan, LLP

(57) ABSTRACT

The system and method for testing a filter containment system. A containment system may include a filter housing with a diverging transition section mounted upstream and a converging transition section mounted downstream. An upstream test section can be arranged upstream of the diverging transition section. During a test of the filter, and aerosol can be dispersed substantially evenly across a cross-sectional area of the upstream test section. The downstream test section can be arranged downstream of the converging transition section. The downstream test section may optionally include a mixer that disturbs the airflow. The downstream test section can also include a sampling array, downstream of the mixer that simultaneously samples the airflow substantially evenly across the cross-sectional area of the downstream test section for the presence of aerosol.

10 Claims, 6 Drawing Sheets

(52) U.S. Cl.
CPC ........ *B01D 2273/18* (2013.01); *G01N 1/2247* (2013.01); *G01N 2001/2223* (2013.01); *G01N 2015/084* (2013.01)

(58) Field of Classification Search
CPC ........... G01N 1/2242; G01N 2001/225; G01N 2001/2223; B01D 2273/18; B01D 65/10; B01D 65/102; B01D 65/104
See application file for complete search history.

(56) References Cited

U.S. PATENT DOCUMENTS

| | | | |
|---|---|---|---|
| 4,548,068 | A | 10/1985 | Gualtieri et al. |
| 5,107,923 | A | 4/1992 | Sherman et al. |
| 8,608,825 | B2 | 12/2013 | Morse et al. |
| 2006/0053864 | A1 | 3/2006 | Morse et al. |
| 2007/0044438 | A1 | 3/2007 | Morse et al. |
| 2009/0056547 | A1 | 3/2009 | Huza et al. |
| 2009/0266064 | A1 | 10/2009 | Zheng et al. |
| 2014/0053634 | A1 | 2/2014 | Woolard et al. |
| 2014/0115852 | A1 | 5/2014 | Morse et al. |

OTHER PUBLICATIONS

Search Report for European Patent Application No. 15846176.4 dated Sep. 29, 2017.

* cited by examiner

CONTAINMENT HOUSING WITH INTEGRATED TEST AEROSOL INJECTION AND SAMPLING

CROSS-REFERENCE TO RELATED APPLICATIONS

This application claims benefit of U.S. Provisional Application Ser. No. 62/059,578, filed Oct. 3, 2014, of which is incorporated by reference in its entirety.

FIELD

Embodiments of the disclosure generally relate to the field of leak testing of filters.

BACKGROUND

FIGS. 1A and 1B depict a conventional containment system 100. A conventional containment system 100 typically includes multiple components arranged in series for filtering air from a ventilation system for a building or other structure, and for testing the integrity and sealing of the filter. The components of the conventional containment system generally includes a diverging transition section 112, an upstream test section 110, a filter housing section 102, a downstream test section 106, and a converging transition section 114. The conventional containment system 100 can be connected in line in a ventilation system for a building or other structure. The diverging transition section 112 can be connected to a ventilation duct via a flange 116, bracket or the like. Similarly, the converging transition section 114 can be connected to a ventilation duct via a flange 118, bracket, or the like. The upstream test section 110 and the downstream test section 106 can include dampers 108 that can be closed to isolate the filter housing section 102 and test equipment arranged between the filter housing 102 and the dampers 108 from the remainder of the ventilation system.

The filter housing section 102 can include one or more doors 104 that allow access to one or more filters, such as HEPA filters, for replacement. After a filter is replaced (and, in some instances, periodically between filter replacements), the filter(s) in the filter housing section 102 are tested to ensure the filter material is intact and the filter is properly seated and sealed in the filter housing 102. To test the filter(s), the dampers 108 are closed to isolate the filter(s), test equipment located in the upstream test section 110, and test equipment in the downstream test section 106 from the ventilation system for the building. A separate source of air can establish airflow from the upstream test section 110, through the filter(s) in the filter housing section 102, and out of the downstream test section 106 for testing the filter(s). In a conventional containment system 100, the upstream test section 110 includes one or more aerosol injection ports that introduce an aerosol into the upstream test section 110. One or more aerosol nozzles in communication with the aerosol injection ports can be arranged in the upstream test section 110 to introduce an aerosol upstream of the filter. The downstream test section 106 can include one or more sensor ports that retrieve air samples downstream from the filter. One or more sensor probes in communication with the one or more sensor ports can be arranged in the downstream test section 106 to sample the air for the presence of the aerosol agent. The sensor probes may be moved in the downstream test section to sample air at different locations in a cross-sectional area such that air passing through the entire downstream face of the filter is sampled. The presence of aerosol in the downstream test section could indicate a leak caused by a failure of the filter material (e.g., a tear, puncture or other leak) or by a failure of a sealing mechanism between the filter and the filter housing. An exemplary conventional containment system is described in U.S. Pat. No. 8,608,825, the contents of which are incorporated by reference herein in its entirety.

SUMMARY

In various embodiments, a filter housing can include a housing that includes an airflow inlet aperture and an airflow outlet aperture. The filter housing can also include a filter sealing portion disposed in the housing between the inlet and outlet apertures, and the airflow inlet aperture and the airflow outlet aperture can include a first cross-sectional area. An upstream diverging transition section can be connected to the airflow inlet aperture. A downstream converging transition section can be connected to the airflow outlet aperture. The filter housing can include a downstream test section that includes an upstream aperture and a downstream aperture. The upstream aperture of the downstream test section can be coupled to a downstream aperture of the downstream converging transition section. The downstream test section can include a mixer arranged relative to the upstream aperture of the downstream test section. The downstream test section can also include an array of sensing ports arranged in the downstream test section between the upstream aperture and the downstream aperture and downstream of the mixer. Each sensing port can be arranged in a different cross-sectional area of the downstream test section. The downstream test section can also include a plurality of aerosol sample ports arranged on a side of the downstream test section between the upstream aperture and the downstream aperture. The aerosol sample ports are in communication with the array of sensing ports.

In various embodiments in which a filter is arranged in a housing between an upstream diverging transition section and a downstream converging transition section, a method for testing the filter can include simultaneously dispersing an aerosol at a plurality of locations in a cross-sectional area of a first duct into an airstream moving toward the filter. The aerosol can be dispersed at a location that is upstream of the diverging transition section. The method can also include disturbing the airstream downstream from the converging transition section. The method can also include simultaneously sampling the airstream downstream from the converging transition section at a plurality of locations in a cross-sectional area of a second duct. The method can also include testing the sampled airstream for the dispersed aerosol.

In various embodiments, a filter housing for a ventilation system can include a housing that includes an airflow inlet aperture and an airflow outlet aperture. The filter housing can also include a filter sealing portion disposed in the housing between the inlet and outlet apertures, and the airflow inlet aperture and the airflow outlet aperture can include a first cross-sectional area. An upstream diverging transition section can be connected to the airflow inlet aperture. A downstream converging transition section can be connected to the airflow outlet aperture. The filter housing can also include an upstream test section that includes an upstream aperture and a downstream aperture. The downstream aperture of the upstream test section can be coupled to an upstream aperture of the upstream diverging transition section. The upstream test section can include a first aerosol sample port arranged on a side of the upstream test section between the upstream aperture and the downstream aperture.

The first aerosol port can be configured to receive a supply of an aerosol testing agent. The upstream test section can include an array of dispersion apertures arranged in the upstream test section between the upstream aperture and the downstream aperture. Each dispersion aperture can be arranged in a different cross-sectional area of the upstream test section. The filter housing can also include a downstream test section that includes an upstream aperture and a downstream aperture. The upstream aperture of the downstream test section can be coupled to a downstream aperture of the downstream converging transition section. The downstream test section can include a mixer arranged relative to the upstream aperture of the downstream test section. The downstream test section can also include an array of sensing ports arranged in the downstream test section between the upstream aperture and the downstream aperture and downstream of the mixer. Each sensing port can be arranged in a different cross-sectional area of the downstream test section. The downstream test section can also include a second aerosol sample port arranged on a side of the downstream test section between the upstream aperture and the downstream aperture. The second aerosol sample port can be in communication with the array of sensing ports.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments.

To facilitate understanding, identical reference numerals have been used, where possible, to designate identical elements that are common to the figures. It is contemplated that elements disclosed in one embodiment may be beneficially utilized in other embodiments without specific recitation.

DETAILED DESCRIPTION

Figure 1A:
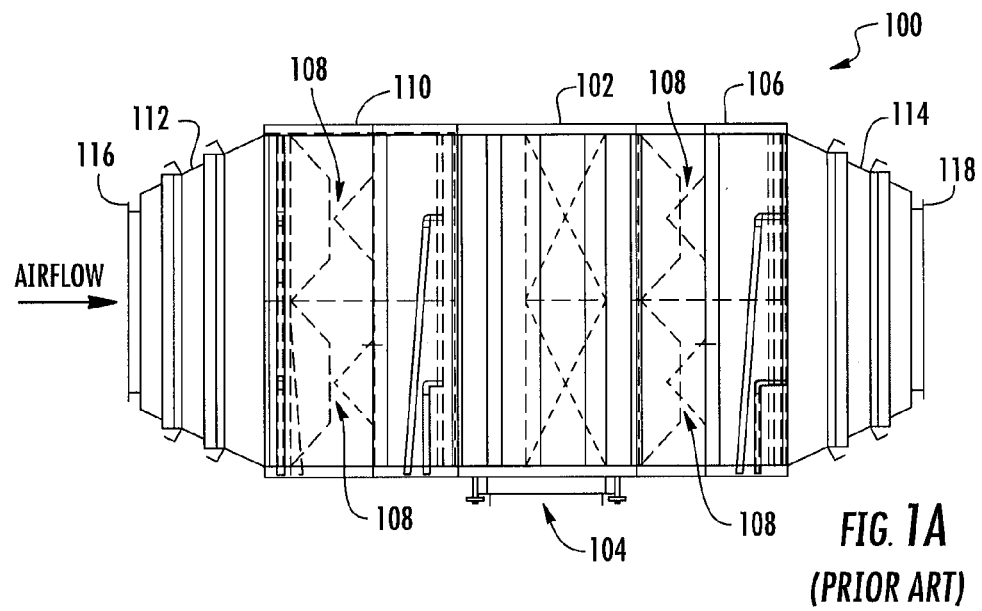
FIG. 1A is a top view of a conventional containment system.
Figure 1B:
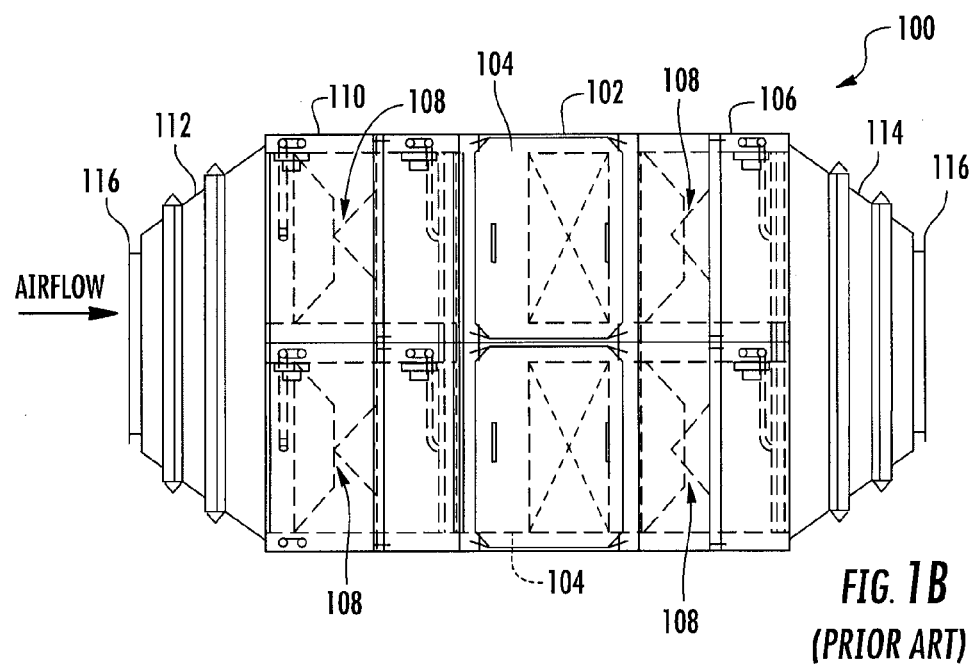
FIG. 1B is a side view of the conventional containment system of FIG. 1A.

In the conventional containment system 100 depicted in FIGS. 1A and 1B, the upstream test section 110 and the downstream test section 106 have approximately the same cross-sectional area as the filter housing section 102. Such large test sections are necessary because the aerosol may not be completely mixed with the airflow. To ensure accurate testing, the aerosol must be mixed sufficiently to have a uniform concentration across the upstream face of the filter. Similarly, samples taken downstream of the filter must also be sufficiently mixed to ensure a statistically valid efficiency test. Generally, for the aerosol to be completely mixed with the surrounding airflow, the aerosol should be introduced into the airflow at a point that is upstream of the location where it needs to be completely mixed (i.e., the filter or downstream sample port) by at least 10 cross-sectional dimensions of the duct through which the airflow is traveling. For example, in a circular duct having a diameter of 14 inches, the aerosol should be injected at a point at least 140 inches upstream from where complete mixing is desired. However, such dimensional requirements can result in a test section that is significantly longer than the conventional containment system 100 shown in FIGS. 1A and 1B, which accordingly undesirably requires a larger foot print along with increased material costs.

Alternatively, baffles or other mixing elements may be disposed in the test sections of the conventional containment system 100 to provide adequate mixing over a shorter length. However, the addition of mixing elements significantly restricts the airflow through the conventional containment system 100. Thus, a larger fan, blower, or the like must be used, which also uses more power to achieve a desired airflow than if such hardware were not present. The larger fan undesirably increases equipment cost, while the increased airflow resistance undesirable consumes more energy, making the system more expensive to operate.

In various embodiments described herein, test sections for a containment system are arranged upstream and downstream of diverging transition sections and converging transition sections, respectively. As a result, the test sections are significantly smaller than the test sections in conventional containment systems, such as conventional containment system 100. Furthermore, in various embodiments described herein, an upstream test section can use a fixed array of aerosol dispersion apertures that can simultaneously and evenly distribute an aerosol across a cross-section of the test section. As a result, the aerosol is almost immediately evenly mixed with the airflow such that the upstream test section can be arranged immediately upstream of the diverging transition section. Also, in various embodiments described herein, a downstream test section can optionally include a mixing apparatus in combination with an array of aerosol sensor ports that simultaneously and evenly sample airflow across a cross-section of the downstream test section. Again, as a result, the downstream test section can be arranged immediately downstream of the converging transition section, allowing for a shorter, less expensive containment system. Furthermore, the hardware in the upstream and downstream can be fixed in place, reducing the amount of hardware in the airflow path and thereby improving the energy efficiency of the containment system, making the containment system less expensive to operate.

Figure 2A:
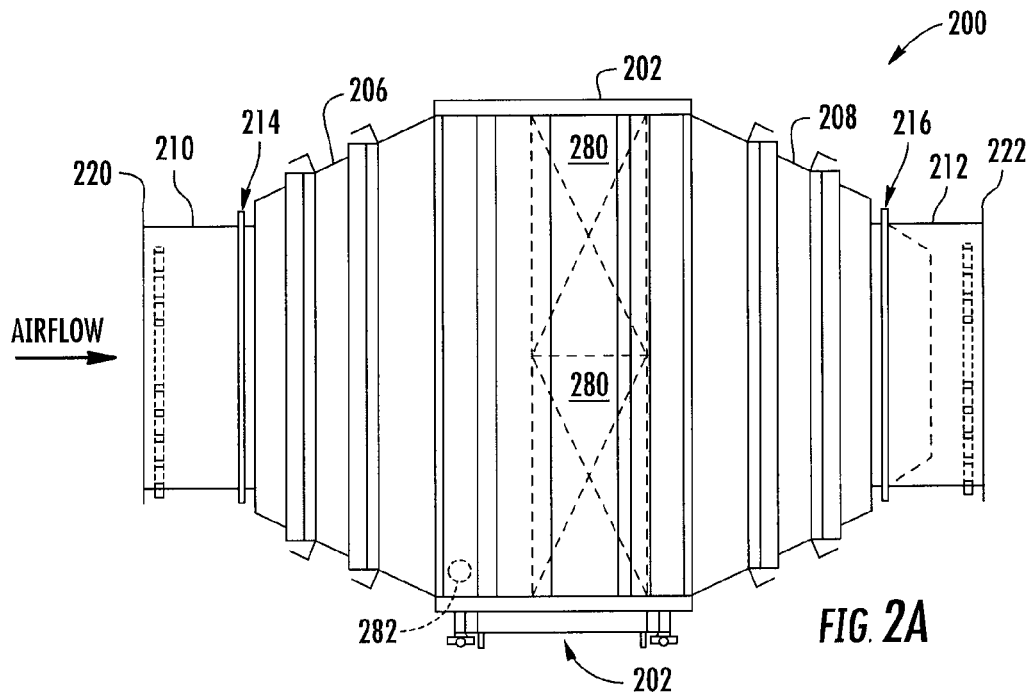
FIG. 2A is a top view of an embodiment of a containment system.
Figure 2B:
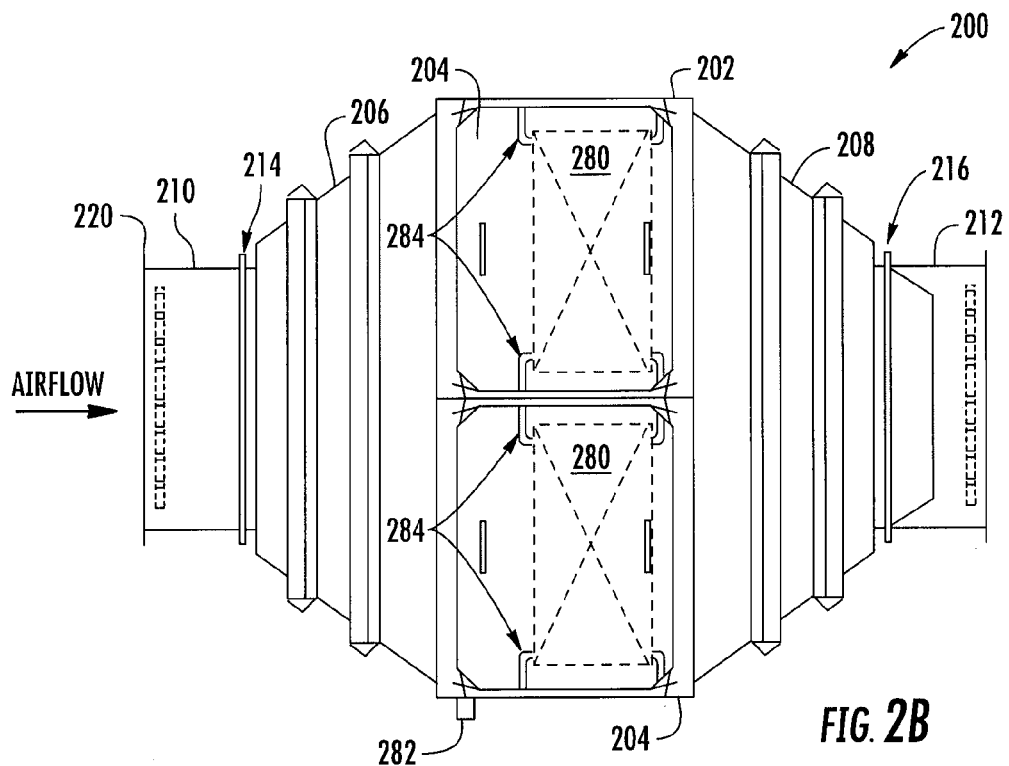
FIG. 2B is a side view of the containment system of FIG. 2A.
Figure 3A:
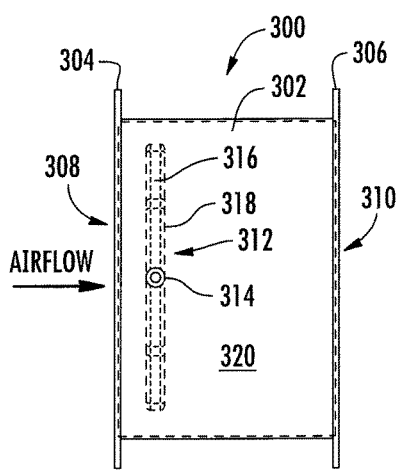
FIG. 3A is a side view of an upstream test section of the containment system of FIG. 2A, wherein interior features are illustrated as hidden lines.
Figure 3D:
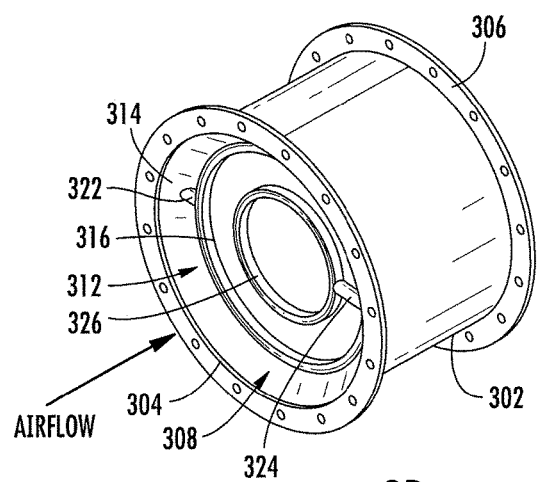
FIG. 3D is a perspective view of the upstream test section of FIG. 3A.
Figure 3B:
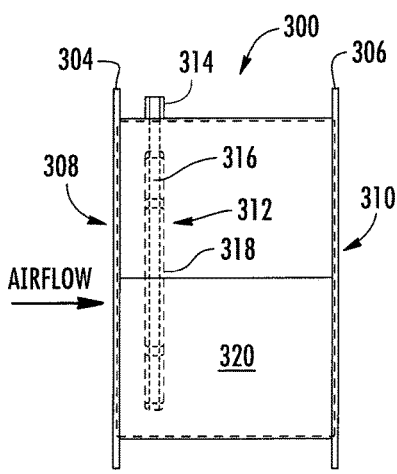
FIG. 3B is a top view of the upstream test section of FIG. 3A.
Figure 3C:
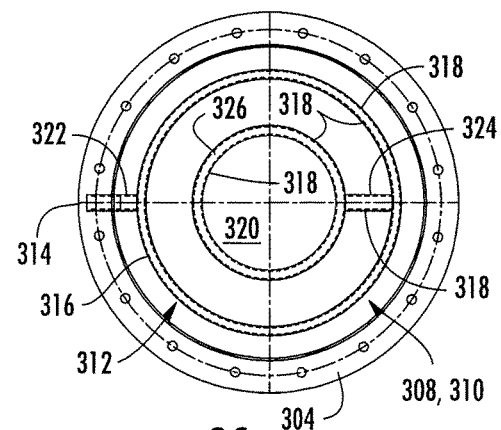
FIG. 3C is an end view of the upstream test section of FIG. 3A.

FIGS. 2A and 2B illustrate a containment system 200 according to various embodiments. The containment system 200 includes a filter housing section 202. The filter housing section 202 includes an airflow inlet aperture and an airflow outlet aperture. The filter housing section 202 can include one or more doors 204 that can be opened to permit access to filters 280 (shown in phantom) contained therein. The filter housing section 202 also includes an upstream sample port 282 formed therethrough to allow samples of the aerosol concentration in the airflow upstream of the filters 280 to be obtained for use during filter testing. The filter housing section 202 also includes a filter mounting mechanism 284 (also shown in phantom) that is substantially aligned with the doors 204, The filter mounting mechanism 284 receives the filters 280 disposed in the filter housing section 202 through the doors 204 and can be actuated to sealingly retain the filters 280 in a position within the filter housing section 202 such that air entering the filter housing section 202 through the airflow inlet aperture and exiting the airflow outlet aperture must pass through and be filtered by the filters 280. The filter mounting mechanism 284 may be any suitable filter clamping mechanism utilized in commercially available containment systems, or other suitable filter clamping system.

The containment system 200 can include a diverging transition section 206 that is in communication with an upstream side and the airflow inlet aperture of the filter housing section 202. The containment system 200 can also include a converging transition section 208 that is in communication with the airflow outlet aperture of the filter housing section 202. The containment system 200 also includes an upstream test section 210 attached to an upstream side of the diverging transition section 206. The containment system 200 also includes a downstream test section 212 attached to a downstream side of the converging transition section 208. The upstream test section 210 can be attached to the diverging transition section 206 at a flange interface 214. Similarly, the downstream test section 212 can be attached to the converging transition section 208 at a flange interface 216.

FIGS. 3A-3D illustrate an embodiment of an upstream test section 300 that could be used in the containment system 200 shown in FIGS. 2A and 2B. The upstream test section 300 could be installed in place of the upstream test section 210 shown in FIGS. 2A and 2B. Any of the descriptions of the upstream test section 210 can also apply to the upstream test section 300 shown in FIGS. 3A-3D. In the embodiment depicted, the upstream test section 300 has a circular cross-sectional shape (to match a circular duct). In various other embodiments, the upstream test section 300 could have a different cross-sectional shape (e.g. square or rectangular) to match a shape of ductwork in a ventilation system. The upstream test section 300 can include an upstream flange 304, a downstream flange 306, and a tubular body 302 therebetween that defines the cross-sectional shape. The upstream flange 304 can be attached to a similar flange on ventilation duct work. Similarly, the downstream flange 306 can be attached to a flange on the upstream end of the diverging transition section 206 (to form the flange interface 214). The tubular body 302 of the upstream test section 300 can form a passageway 320 extending from an upstream aperture 308 to a downstream aperture 310. The upstream test section 300 can also include an aerosol nozzle array tube 312 arranged in the passageway 320. The aerosol nozzle array tube 312 can be connected to and in fluid communication with an aerosol port 314 arranged through the tubular body 302. The aerosol nozzle array tube 312 can be formed into two or more rings that are arranged across the cross-sectional profile of the passageway 320. For example, the aerosol nozzle array tube 312 depicted in FIGS. 3A-3D includes an outer ring 316 and an inner ring 326 that are arranged concentrically relative to one another. The outer ring 316 and the inner ring 326 may also be arranged concentrically with the passageway 320. The outer ring 316 can be connected to the aerosol port 314 by a first radially extending tube portion 322. The inner ring 326 can be connected to the outer ring 316 by a second radially extending tube portion 324. Aerosol can be introduced into the aerosol port 314 and can travel through the first radially extending tube portion 324 to the outer ring 316. At the outer ring 316, the aerosol can then split in two directions to travel through the portions of the tube 312 that make up the outer ring 316. The aerosol can then travel through the second radially extending tube portion 324 to the inner ring 326. Again, the aerosol can then split into directions to travel to the portions of the tube 312 that make up the inner ring 326. The opposite positions of the first and second radially extending tube portions 322, 324 helps evenly distribute the aerosol within the rings 326, 316. The inner ring 326 and the outer ring 316 can include an array of apertures 318 through which aerosol can exit from the aerosol nozzle array tube 312 and enter the passageway 320 mix with the airflow. In various embodiments, the first radially extending tube portion 324 and/or the second radially extending tube portion 324 can also include one or more apertures 318.

In various embodiments, the array of apertures 318 can be arranged on surfaces of the aerosol nozzle array tube 312 that face radially inward and radially outward (i.e., perpendicular to the general direction of airflow). In various embodiments, the array of apertures 318 can be arranged such that each aperture is in communication with a substantially equal cross-sectional area of the passageway 320 such that aerosol is distributed into the airflow evenly across the cross-sectional area of the passageway 320. In various other embodiments, the array of apertures 318 can be arranged such that the flow of aerosol from the array of apertures 318 is substantially even across the cross-sectional area of the passageway 320. For example, if a substantial pressure gradient is present in the aerosol nozzle array tube 312 from the aerosol port 314 to the inner ring 326, more nozzles may need to be arranged in the inner ring 326 then the outer ring 316 to evenly distribute the aerosol into the passageway 320. To minimize pressure gradients in the aerosol nozzle array tube 312, in various embodiments, the sum of the cross-sectional areas of the apertures 318 may be substantially equal to an interior cross-sectional area of the aerosol nozzle array tube 312. Reducing the pressure gradient can provide for more even flow of aerosol through the apertures 318 and therefore more even distribution of aerosol across the cross-sectional area of the passageway 320. As used herein, substantially equal can provide for a difference of up to 10%.

FIGS. 4A-4F illustrates an embodiment of a downstream test section 400 that could be used in the containment system 200 shown in FIGS. 2A and 2B. The downstream test section 400 could be installed in place of the downstream test section 212 shown in FIGS. 2A and 2B. Any of the descriptions of the downstream test section 212 can also apply to the downstream test section 400 shown in FIGS. 4A-4F. In the embodiment depicted, the downstream test section 400 has a circular cross-sectional shape (to match a circular duct). In various other embodiments, the downstream test section 400 can have a different cross-sectional shape (e.g., square or rectangular) to match a shape of ductwork in a ventilation system. The downstream test section 400 can include an upstream flange 404, a downstream flange 406, and a tubular body 402 therebetween that defines the cross-sectional shape. The upstream flange 404 can be attached to a flange on the downstream end of the converging transition section 208 (to form the flange interface 216). Similarly, the downstream flange 406 can be attached to a similar flange on ventilation duct work. The tubular body 402 of the downstream test section 400 can form a passageway 420 extending from an upstream aperture 408 to a downstream aperture 410. The downstream test section 400 can also include an aerosol sampling array tube 440 arranged in the passageway 420. The aerosol sampling array tube 440 can be connected to and in fluid communication with an aerosol sampling ports 442 arranged through the tubular body 402. The aerosol sampling array tube 440 can be formed into one or more rings that are arranged relative to the passageway 420. For example, the aerosol sampling array tube 440 depicted in FIGS. 4A-4F includes an outer ring 444 and an inner ring 448 that are arranged concentrically relative to one another. The outer ring 444 can be connected to the aerosol sampling port 442 by a first radially extending tube portion 450. The inner ring 448 can be connected to the outer ring 444 by a second radially extending tube portion 452. The aerosol sampling port 442 can be connected to a vacuum source (e.g., a pump) that draws air from the passageway 420 through apertures 446 in the aerosol sampling array tube 440. Air entering the aerosol sampling array tube 440 through apertures 446 in the outer ring 444 can pass through the second radially extending tube portion 452 into the inner ring 448. Air entering the aerosol sampling array tube 440 through apertures 446 in the inner ring 448 can mix with air traveling through the aerosol sampling array tube 440 from the outer ring 444 and can pass through the first radially extending tube portion 450. In various embodiments, the first radially extending tube portion 450 and/or the second radially extending tube portion 452 can also include apertures 446 through which air from the passageway 420 enters the aerosol sampling array tube 440. The air from the aerosol sampling ports 442 can then be tested via leak testing equipment, such as particle counters, photometers, and the like, for the presence of aerosol, which may indicate a leak through the filter or sealing between the filter 280 and the filter mounting mechanism 284. In one embodiment, the air from the aerosol sampling ports 442 is provided along with air from the upstream sample port 282 to the leak testing equipment to determine the overall filtration efficiency of the filter 280.

In various embodiments, the array of apertures 446 can be arranged on surfaces of the aerosol sampling array tube 440 that face one or both of radially inward and radially outward (i.e., perpendicular to the general direction of airflow). The array of apertures 446 can alternatively face other directions. In various embodiments, the array of apertures 446 can be arranged on the aerosol sampling array tube 440 such that each aperture is in communication with a substantially equal cross-sectional area of the passageway 420 such that the airflow is evenly sampled across the cross-sectional area of the passageway 420, which enables obtaining accurate testing results. In various other embodiments, the array of apertures 446 can be arranged on the aerosol sampling array tube 440 such that the flow of the airflow from the passageway 420 into the array of apertures 446 is substantially even across the cross-sectional area of the passageway 420. For example, if a substantial pressure gradient is present in the aerosol sampling array tube 440 from the inner ring 448 to the aerosol sampling port 442, more nozzles may need to be arranged in the inner ring 448 (where a pressure vacuum across the apertures 446 is lowest) than the outer ring 444 (where the pressure vacuum across the apertures 446 is higher) to evenly sample the airflow from the passageway 420. To minimize pressure gradients in the aerosol sampling array tube 440, in various embodiments, the sum of the cross-sectional areas of the apertures 446 is substantially equal to an interior cross-sectional area of the aerosol sampling array tube 440. Reducing the pressure gradient can provide for more even flow amongst the apertures 446 and therefore more even sampling of airflow across the cross-sectional area of the passageway 420. As used herein, substantially equal can provide for a difference of up to 10%.

The downstream test section 400 can also include a mixer 470 arranged upstream of the aerosol sampling array tube 440. The mixer can disturb the airflow of air coming from the converging transition section 208 to ensure that the airflow being sampled by the aerosol sampling array tube 440 is homogenous. The mixer 470 may be a static mixer, such as vanes, disk or diffusers; a dynamic mixer, such as moving blades or vanes; or a combination thereof. In various embodiments, the mixer 470 can include a first portion 430 that directs air from outer portions of the passageway 420 radially inward, which induces turbulent flow and good mixing without significant back pressure generation. The mixer 470 may optionally also include a second portion 460 that directs air from center portions of the passageway 420 radially outward to enhance mixing. The first portion 430 may be utilized alone or in combination with the second portion 460, or vice versa. In the embodiment shown in FIGS. 4A-4F, the first portion 430 includes a conical surface 432 arranged at the upstream aperture 408 of the downstream test section 400. The first portion 430 can terminate with an aperture 434 that is smaller than the upstream aperture 408 of the downstream test section 400. The first portion 430 of the mixer 470 can direct air entering the downstream test section 400 near the tubular body 402 of the downstream test section 400 radially inward toward the center of the passageway 420. In the embodiment shown in FIGS. 4A-4F, the second portion 460 includes an array of apertures 466 through a disk 480 (e.g., a plate with perforations therethrough). The disk and array of apertures 466 are arranged in a circular shape in FIGS. 4A-4F, but could be arranged in other shapes (e.g., a square, rectangle, or a polygon). The apertures 466 allow air in the center of the passageway 420 to pass there through. However, the apertures 466 also restrict the airflow, causing some of the air passing from near the center of the converging transition section 208 into the downstream test section 400 to go around the second portion 460, translating radially outward toward the tubular body 402 of the downstream test section 400. In various embodiments, the apertures 466 can be of different sizes at different locations. For example, in certain embodiments, the apertures 466 toward the center 464 of the array may be smaller than apertures 466 toward an outside 462 of the array. Such an arrangement of apertures may direct more airflow radially outward. In certain other embodiments, the apertures 466 toward the center 464 of the array may be larger than apertures 466 toward the outside 462 of the array. The second portion 460 can be supported in the passageway 420 by a support member 468. As shown in FIGS. 4A-4F, in various embodiments, the second portion 460 of the mixer 470 can be arranged approximately flush with the upstream aperture 408 of the downstream test section 400.

The first portion 430 and the second portion 460 of the mixer 470 can work in concert to mix the airflow from the converging transition section 208. The first portion 430 and the second portion 460 of the mixer 470 can be arranged so that airflow moving radially inward in the passageway 420 (from the first portion 430 of the mixer 470) interacts with airflow moving radially outward in the passageway 420 (from the second portion 460 of the mixer 470). Such interaction of airflow can disturb the airflow, creating turbulence that can distribute any local concentration of aerosol. For illustration purposes, as an example, during a test, aerosol may leak through a pin hole leak present in the edge of the filter proximate the filter mounting mechanism 284. Such a leak may result in a localized flow of aerosol past the filter and along a wall in the filter housing section 202. The localized flow of aerosol may then travel along a wall of the converging transition section 208. At the downstream test section 400, the localized flow of aerosol would be diverted radially inward by the first portion 430 of the mixer 470. Then, the interaction of radially inward and radially outward airflow from the first portion 430 and second portion 460, respectively, of the mixer 470 would disperse the localized aerosol flow into a larger volume of air which has been filtered to remove the aerosol by passing through the filter 280. By disturbing the localized flow of aerosol into the larger volume of filtered air, the aerosol sampling array tube 440 could more accurately obtain a sample representative of the amount of aerosol reaching the downstream side of the filter 280, commonly referred to as an overall filtration efficiency test. Should the sample be solely taken using the localized aerosol flow, the overall filtration efficiency test who erroneously indicate a lower than actual filtration efficiency. Thus, the mixer enhances the accuracy of test results.

Figure 4A:
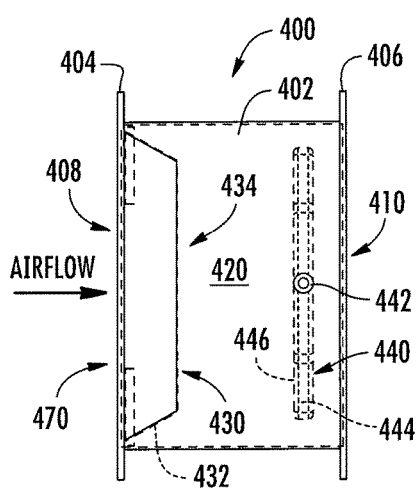
FIG. 4A is a side view of a downstream test section of the containment system of FIG. 2A, wherein interior features are illustrated as hidden lines.
Figure 4D:
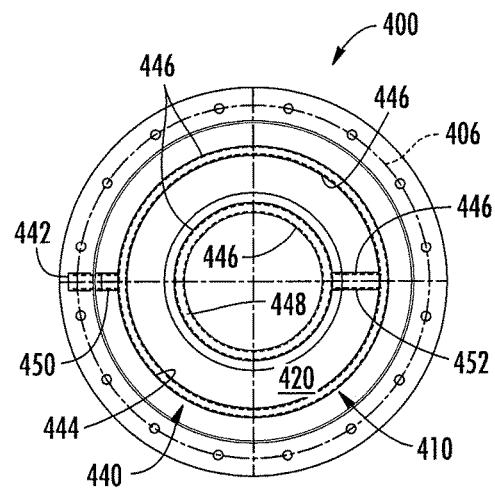
FIG. 4D is an end view of the downstream end of the downstream test section of FIG. 4A.
Figure 4B:
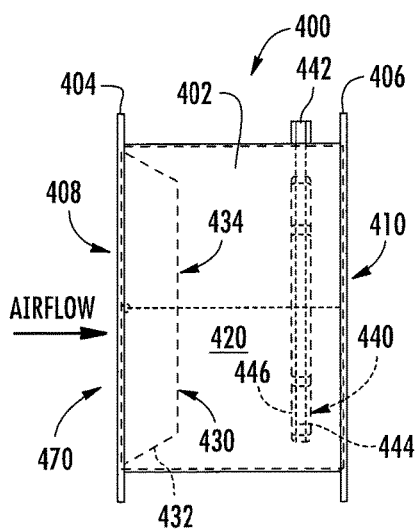
FIG. 4B is a top view of the downstream test section of FIG. 4A.
Figure 4C:
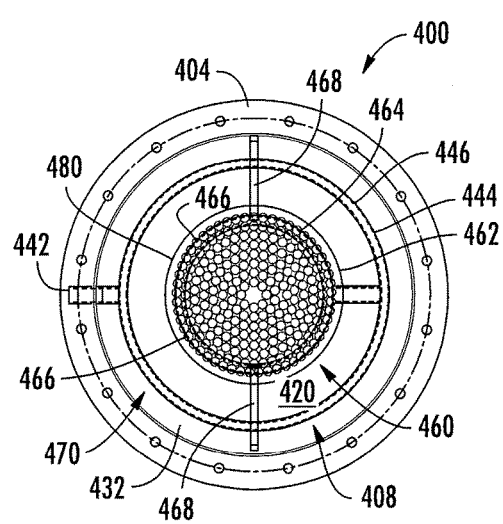
FIG. 4C is an end view of the upstream end of the downstream test section of FIG. 4A.
Figure 4E:
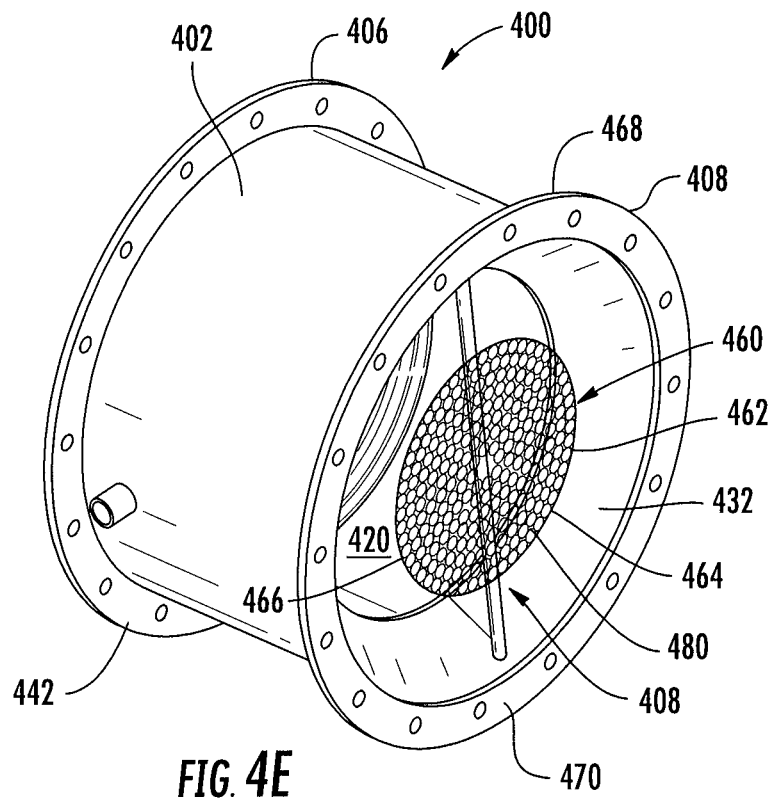
FIG. 4E is a perspective view looking at the upstream end of the downstream test section of FIG. 4A.
Figure 4F:
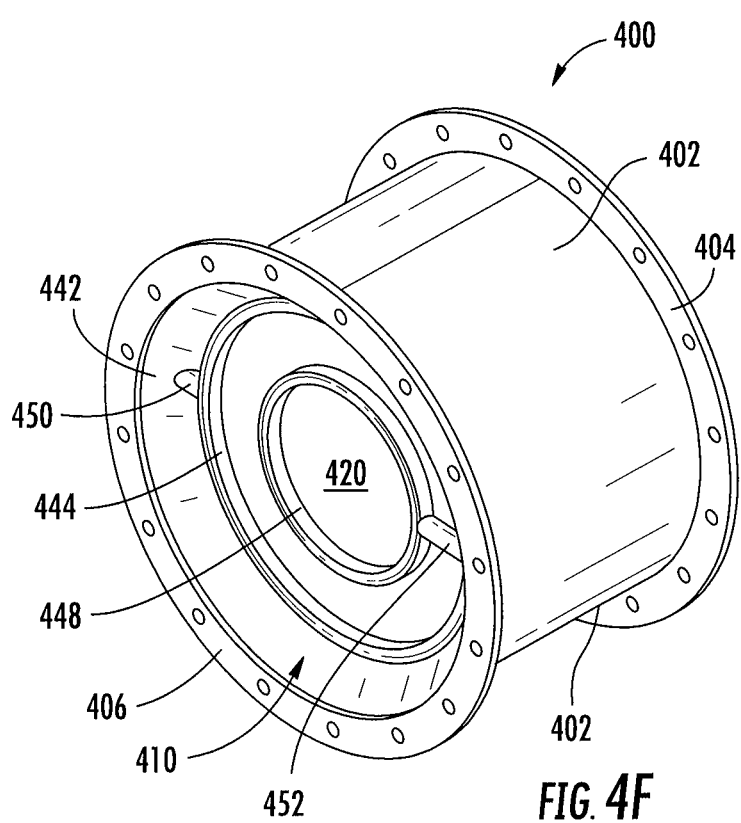
FIG. 4F is a perspective view looking at the downstream end of the downstream test section of FIG. 4A.
Figure 4G:
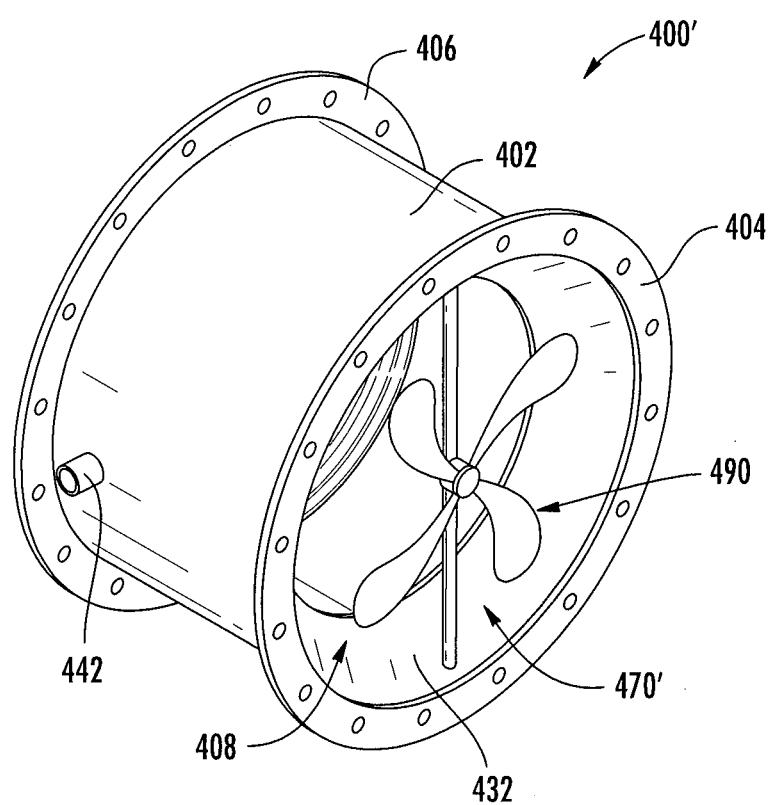
FIG. 4G is a perspective view looking at the upstream end of another embodiment of a downstream test section.

FIG. 4G illustrates an alternative embodiment of a downstream test section 400' that includes a different second portion of the mixer 470'. In the downstream test section 400' in FIG. 4G, the second portion 490 is shaped like a static vane. The static vane can diverts airflow radially outward. In addition, surfaces of the static vane can introduce rotation to the airflow, which can also divert the airflow radially outward. Such rotation of the airflow can also further enable mixing of the airflow by adding a circular airflow velocity component to the radially inward and radially outward airflow velocity components discussed above.

In various embodiments, the aerosol nozzle array tube 312 and the aerosol port 314 in the upstream test section 300 can be arranged toward the upstream aperture 308. As discussed above, the aerosol nozzle array tube 312 distributes the aerosol substantially evenly in a cross-sectional shape of the tubular body 302. To promote more homogeneous distribution of the aerosol in the air stream at the upstream face of the filter 280, the aerosol nozzle array tube 312 may be located preferentially toward the upstream end of the upstream test section 300, thus increasing the distance the aerosol can continue to disperse as it travels the remaining length of the passageway 320 in the upstream test section 300, thereby allowing greater time and distance to achieve a uniform aerosol concentration across the air flow at the upstream face of the filter 280. Similarly, in various embodiments, the aerosol sampling array tube 440 and the aerosol sampling ports 442 in the downstream test section 400 can be arranged toward the downstream aperture 410. As discussed above, the mixer 470 at the upstream aperture 408 of the downstream test section 400 can mix the incoming airflow so that any aerosol that leaked past the filter is substantially evenly mixed. By arranging the aerosol sampling array tube 440 toward the downstream end of the downstream test section 400, any aerosol can continue to disperse as it travels the remaining length of the passageway 420 in the downstream test section 400, thereby allowing greater time and distance to achieve a representative aerosol concentration in the filtered air downstream of the filter 280, and accordingly facilitating more accurate filter efficiency testing results.

In the embodiments of the upstream test section 300 and the downstream test section 400 shown in FIGS. 3A-3D and FIGS. 4A-4G, respectively, the aerosol nozzle array tube 312 and the aerosol sampling array tube 440 are each depicted as two concentric rings. In various embodiments, the aerosol nozzle array tube 312 and the aerosol sampling array tube 440 may include more or fewer rings. For example, larger diameter test sections may include tubes formed into three, four, or more concentric rings. Similarly, smaller diameter test sections may include tubes formed into a single ring. In various embodiments, the test sections may not have a circular cross-sectional shape. In such embodiments, the tubes may be formed into a shape or shapes that match the cross-sectional shape of the test sections. For example, if the test sections have a rectangular cross-sectional shape, then the tubes may be formed into rectangular shapes in the passageways.

As discussed above, embodiments of test sections described in FIGS. 3A-3D and 4A-4F can provide for a substantially homogenous distribution of an aerosol upstream of the filter and also downstream of the filter for sampling purposes, thereby enabling accurate and reliable filter efficiency testing result. Furthermore, such embodiments of test sections could result in a lower pressure drop across the containment system 200, thereby reducing the power requirements for the ventilation system as a whole. In addition, the resulting containment system 200 can be more compact than conventional containment systems, such as containment system 100 shown in FIGS. 1A and 1B. For example, embodiments of the conventional containment system 100 have a length from the upstream flange 116 on the diverging transition section 112 to the downstream flange 118 on the converging transition section 114 of one hundred and fifteen inches. By contrast, embodiments of the containment system 200 have a link from the upstream flange 220 of the upstream test section 210 to the downstream flange 222 of the downstream test section 212 of eighty five inches. Such length reductions could result in a containment system 200 that requires less floor space than the conventional containment system 100, and is less expensive to build and operation.

In addition to the examples described above, some additional non-limiting examples may be described as follows:

Example 1

A containment apparatus, comprising:
a housing comprising an airflow inlet aperture and an airflow outlet aperture;
a filter sealing portion disposed in the housing between the inlet and outlet apertures;
an upstream diverging transition section connected to the airflow inlet aperture;
a downstream converging transition section connected to the airflow outlet aperture;
a downstream test section that includes an upstream aperture and a downstream aperture, the upstream aperture of the downstream test section configured to be coupled to a downstream aperture of the downstream converging transition section, the downstream test section comprising:
- an array of sensing ports arranged in the downstream test section between the upstream aperture and the downstream aperture, wherein each sensing port is arranged in a different cross-sectional area of the downstream test section; and
- an aerosol sample port arranged on a side of the downstream test section between the upstream aperture and the downstream aperture, wherein the aerosol sample port is in communication with the array of sensing ports.

Example 2

The containment apparatus of example 1, further comprising a mixer arranged relative to the upstream aperture of the downstream test section, and wherein the array of sensing ports is arranged downstream of the mixer.

Example 3

The containment apparatus of example 2, wherein the mixer comprises:
- a converging portion arranged relative to the upstream aperture of the downstream test section.

Example 4

The containment apparatus of example 3, wherein the mixer further comprises a baffle arranged at the upstream aperture of the downstream test section.

Example 5

The containment apparatus of example 4, wherein the baffle comprises a perforated disk, wherein a center of the perforated disk is substantially aligned with a center of the downstream test section.

Example 6

The containment apparatus of example 5, wherein the perforations in the perforated disk are smaller toward the center and larger toward the edges of the disk.

Example 7

The containment apparatus of example 4, wherein the baffle comprises a static vane.

Example 8

The containment apparatus of example 1, wherein the downstream test section includes a circular cross-sectional shape, and wherein the array of sensing ports comprises:
- a tube in communication with the aerosol sample port, wherein the tube is shaped into a at least one ring that is arranged substantially concentrically in the upstream test section, wherein the tube further comprises a first radially extending portion in communication with the aerosol sample port and the tube, and wherein the tube includes a plurality of apertures therethrough.

Example 9

The containment apparatus of example 8, wherein the plurality of apertures are arranged on radially-inward-facing and radially-outward-facing surfaces of the tube.

Example 10

The containment apparatus of example 8, wherein a cross-sectional area of the tube is substantially equal to a sum of cross-sectional areas of the plurality of apertures.

Example 11

The containment apparatus of example 8, wherein the tube comprises a first ring and a second ring, wherein the first ring is smaller than the second ring, wherein the first ring and the second ring are arranged substantially concentrically with respect to each other, wherein the tube further comprises a second radially extending portion in communication with the first ring and the second ring.

Example 12

A method for testing a filter, wherein the filter is arranged in a housing between an upstream diverging transition section and a downstream converging transition section, the method comprising:
- upstream of the diverging transition section, simultaneously dispersing an aerosol at a plurality of locations in a cross-sectional area of a first duct in an airflow moving toward the filter;
- filtering the aerosol laden airstream with the filter;
- downstream of the converging transition section:
  - simultaneously sampling the airflow at a plurality of locations in a cross-sectional area of a second duct; and
  - determining an efficiency of the filter utilizing the sampled airflow.

Example 13

The method of example 12, further comprising, downstream of the converging transition section, disturbing the filtered airflow exiting from the converging transition section, and wherein simultaneously sampling the airflow comprises simultaneously sampling the disturbed airflow.

Example 14

The method of example 13, wherein disturbing the airstream from the converging transition section comprises disturbing the airstream at a location that is immediately downstream of the downstream converging transition section.

Example 15

The method of example 13, wherein sampling the disturbed airstream at a plurality of locations comprises sampling the disturbed airstream at a plurality of locations that are less than one foot downstream from the downstream converging transition section.

Example 16

The method of example 12, wherein simultaneously dispersing the aerosol at a plurality of locations in a cross-sectional area of a first duct comprising at a location that is less than one foot upstream from the upstream diverging transition section.

Example 17

A containment system for a ventilation system, comprising:
a housing comprising an airflow inlet aperture and an airflow outlet aperture;
a filter sealing portion disposed in the housing between the inlet and outlet apertures, wherein the airflow inlet aperture and the airflow outlet aperture include a first cross-sectional area;
an upstream diverging transition section connected to the airflow inlet aperture;
a downstream converging transition section connected to the airflow outlet aperture;
an upstream test section that includes an upstream aperture and a downstream aperture, the downstream aperture of the upstream test section configured to be coupled to an upstream aperture of a diverging transition section, the upstream test section comprising:
 a first aerosol sample port arranged on a side of the upstream test section between the upstream aperture and the downstream aperture, wherein the first aerosol port is configured to receive a supply of an aerosol testing agent; and
 an array of dispersion apertures in communication with the first aerosol sample port and arranged in the upstream test section between the upstream aperture and the downstream aperture, wherein each dispersion aperture is arranged in a different cross-sectional area of the upstream test section; and
a downstream test section that includes an upstream aperture and a downstream aperture, the upstream aperture of the downstream test section configured to be coupled to a downstream aperture of a converging transition section, the downstream test section comprising:
 a mixer arranged at the upstream aperture of the downstream test section;
 an array of sensing ports arranged in the downstream test section between the upstream aperture and the downstream aperture and downstream of the mixer, wherein each sensing port is arranged in a different cross-sectional area of the downstream test section; and
 a second aerosol sample port arranged on a side of the downstream test section between the upstream aperture and the downstream aperture, wherein the second aerosol sample port is in communication with the array of sensing ports.

Example 18

The containment system of example 17, wherein the mixer comprises:
 a converging portion arranged relative to the upstream aperture of the downstream test section.

Example 19

The containment system of example 18, wherein the mixer further comprises a perforated plate, wherein a center of the perforated plate is substantially aligned with a center of the downstream test section.

Example 20

The containment system of example 19, wherein the perforations in the perforated plate are smaller toward the center and larger toward the edges of the plate.

Example 21

The containment system of example 17, wherein the mixer further comprises a static vane.

Example 22

The containment system of example 17, wherein the upstream test section includes a circular cross-sectional shape, and wherein the array of dispersion apertures comprises:
 a tube in communication with the first aerosol sample port, wherein the tube is shaped into a at least one ring that is arranged substantially concentrically in the upstream test section, wherein the tube further comprises a first radially extending portion in communication with the first aerosol sample port and the tube, and wherein the tube includes a plurality of apertures therethrough.

Example 23

The containment system of example 22, wherein the plurality of apertures are arranged on radially-inward-facing and radially-outward-facing surfaces of the tube.

Example 24

The containment system of example 22, wherein a cross-sectional area of the tube is substantially equal to a sum of cross-sectional areas of the plurality of apertures.

Example 25

The containment system of example 22, wherein the tube comprises a first ring and a second ring, wherein the first ring is smaller than the second ring, wherein the first ring and the second ring are arranged substantially concentrically with respect to each other, wherein the tube further comprises a second radially extending portion in communication with the first ring and the second ring.

Example 26

The containment system of example 17, wherein the downstream test section includes a circular cross-sectional shape, and wherein the array of sensing ports comprises:
 a tube in communication with the second aerosol sample port, wherein the tube is shaped into a at least one ring that is arranged substantially concentrically in the upstream test section, wherein the tube further comprises a first radially extending portion in communication with the second aerosol sample port and the tube, and wherein the tube includes a plurality of apertures therethrough.

Example 27

The containment system of example 26, wherein the plurality of apertures are arranged on radially-inward-facing and radially-outward-facing surfaces of the tube.

Example 28

The containment system of example 26, wherein a cross-sectional area of the tube is substantially equal to a sum of cross-sectional areas of the plurality of apertures.

Example 29

The containment system of example 26, wherein the tube comprises a first ring and a second ring, wherein the first ring is smaller than the second ring, wherein the first ring and the second ring are arranged substantially concentrically with respect to each other, wherein the tube further comprises a second radially extending portion in communication with the first ring and the second ring.

While the foregoing is directed to embodiments of the present disclosure, other and further embodiments of the disclosure may be devised without departing from the basic scope thereof, and the scope thereof is determined by the claims that follow.

We claim:

1. A downstream test section comprising:
   a tubular body having a circular cross-sectional shape, an upstream aperture and a downstream aperture;
   an array of sensing ports arranged in a passageway of the body between the upstream aperture and the downstream aperture, wherein each sensing port is arranged in a different cross-sectional area of the body, the array of sensing ports comprising:
      a tube in communication with the aerosol sample port, the tube shaped into at least one ring arranged substantially concentric to the body, the tube further comprising:
         a first radially extending portion in communication with the aerosol sample port and at least one ring of the tube, wherein the tube includes a plurality of apertures therethrough which function as the array of sensing ports; and
   an aerosol sample port arranged on a side of the body between the upstream aperture and the downstream aperture, wherein the aerosol sample port is in fluid communication with the array of sensing ports.

2. The downstream test section of claim 1, further comprising:
   a mixer in the body between the array of sensing ports and the upstream aperture.

3. The downstream test section of claim 2, wherein the mixer comprises:
   a converging portion.

4. The downstream test section of claim 3, wherein the mixer further comprises:
   a baffle.

5. The downstream test section of claim 4, wherein the mixer baffle comprises:
   a perforated disk substantially aligned with the center of the body.

6. The downstream test section of claim 5, wherein perforations near a center of the perforated disk are smaller than perforations proximate an edge of the perforated disk.

7. The downstream test section of claim 4, wherein the baffle comprises:
   a static vane.

8. The downstream test section of claim 1, wherein the plurality of apertures are arranged on radially-inward-facing and radially-outward-facing surfaces of the tube.

9. The downstream test section of claim 1, wherein a cross-sectional area of the tube is substantially equal to a sum of cross-sectional areas of the plurality of apertures.

10. The downstream test section of claim 1, wherein the at least one ring tube comprises:
    a first ring and a second ring, wherein the first ring is smaller than the second ring, wherein the first ring and the second ring are substantially concentric, and wherein the tube further comprises:
       a second radially extending portion in communication with the first ring and the second ring.

* * * * *

UNITED STATES PATENT AND TRADEMARK OFFICE
CERTIFICATE OF CORRECTION

PATENT NO. : 10,006,848 B2  
APPLICATION NO. : 14/871250  
DATED : June 26, 2018  
INVENTOR(S) : Keith G. Woolard and Larry E. Bland, Jr.

Page 1 of 1

It is certified that error appears in the above-identified patent and that said Letters Patent is hereby corrected as shown below:

In the Claims

In Column 16, Line 18, in Claim 5 after "the" delete "mixer", therefor.

In Column 16, Line 34, in Claim 10 after "ring" delete "tube", therefor.

Signed and Sealed this  
Twenty-eighth Day of May, 2019

Andrei Iancu  
*Director of the United States Patent and Trademark Office*